United States Patent
Howard et al.

(10) Patent No.: US 10,729,542 B2
(45) Date of Patent: Aug. 4, 2020

(54) STENTED PROSTHETIC HEART VALVE HAVING A PARAVALVULAR SEALING WRAP

(71) Applicant: Medtronic Vascular, Inc., Santa Rosa, CA (US)

(72) Inventors: Elliot Howard, Redwood City, CA (US); Amy Hallak, Laguna Hills, CA (US); Ana Menk, Shoreview, MN (US); Matthew Weston, Roseville, MN (US); Joel Racchini, Edina, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1 day.

(21) Appl. No.: 15/792,991

(22) Filed: Oct. 25, 2017

(65) Prior Publication Data
US 2018/0110617 A1    Apr. 26, 2018

Related U.S. Application Data

(60) Provisional application No. 62/412,875, filed on Oct. 26, 2016.

(51) Int. Cl.
*A61F 2/24* (2006.01)

(52) U.S. Cl.
CPC ............ *A61F 2/2418* (2013.01); *A61F 2/243* (2013.01); *A61F 2/2412* (2013.01); *A61F 2/2409* (2013.01);
(Continued)

(58) Field of Classification Search
CPC ................. A61F 2/2412; A61F 2/2418; A61F 2250/0069
See application file for complete search history.

(56) References Cited

U.S. PATENT DOCUMENTS 5,957,949 A    9/1999 Leonhardt et al.
6,730,118 B2 *  5/2004 Spenser ............... A61F 2/2412
                                                       623/1.24
(Continued)

FOREIGN PATENT DOCUMENTS

EP          2918247 A1    9/2016
WO    WO 2011 109801 A2    9/2011
WO    WO 2015 126711 A1    8/2015

OTHER PUBLICATIONS

PCT communication dated Jan. 28, 2018 in corresponding PCT Appln.No. PCT/US2017/058265.

*Primary Examiner* — Suba Ganesan
(74) *Attorney, Agent, or Firm* — Dicke, Billig & Czaja, PLLC

(57) ABSTRACT

Stented prosthetic heart valves including a stent frame having a plurality of stent frame support structures collectively defining an interior surface, an exterior surface and a plurality of cells. The stented prosthetic heart valve further including a valve structure including valve leaflets disposed within and secured to the stent frame and defining a margin of attachment. The stented prosthetic heart valve including one or both of an outer paravalvular leakage prevention wrap and an inner skirt for supporting the valve leaflets. In various embodiments, the outer wrap is positioned entirely on one side of the margin of attachment. In embodiments including an inner skirt, the outer wrap and the inner skirt are on opposite sides of the margin of attachment such that the inner skirt and the outer wrap do not overlap. In other embodiments, the outer wrap includes a plurality of zones having varying thickness.

20 Claims, 4 Drawing Sheets

(52) U.S. Cl.
  CPC ............ *A61F 2220/0075* (2013.01); *A61F 2250/0069* (2013.01)

(56) References Cited

U.S. PATENT DOCUMENTS

| | | |
|---|---|---|
| 8,579,963 B2 | 11/2013 | Tabor |
| 8,808,356 B2 | 8/2014 | Braido |
| 2003/0199963 A1 | 10/2003 | Tower et al. |
| 2003/0199971 A1 | 10/2003 | Tower et al. |
| 2005/0137682 A1 | 6/2005 | Justino |
| 2013/0197631 A1 | 8/2013 | Bruchman |
| 2015/0073545 A1* | 3/2015 | Braido ............ A61F 2/2412 623/2.18 |

\* cited by examiner

STENTED PROSTHETIC HEART VALVE HAVING A PARAVALVULAR SEALING WRAP

BACKGROUND

The present disclosure relates to stented prosthetic heart valves having a paravalvular sealing wrap.

A human heart includes four heart valves that determine the pathway of blood flow through the heart: the mitral valve, the tricuspid valve, the aortic valve, and the pulmonary valve. The mitral and tricuspid valves are atrioventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, depending on the severity of the disease, and can have significant physiological consequences for the patient.

Recently, flexible prosthetic valves supported by stent structures that can be delivered percutaneously using a catheter-based delivery system have been developed for heart and venous valve replacement. These prosthetic valves may include either self-expanding or balloon-expandable stent structures with valve leaflets attached to the interior of the stent structure. The prosthetic valve can be reduced in diameter, by crimping onto a balloon catheter or by being contained within a sheath component of a delivery catheter, and advanced through the venous or arterial vasculature. Once the prosthetic valve is positioned at the treatment site, for instance within an incompetent native valve, the stent structure may be expanded to hold the prosthetic valve firmly in place. One example of a stented prosthetic valve is disclosed in U.S. Pat. No. 5,957,949 to Leonhardt et al. entitled "Percutaneous Placement Valve Stent." Another example of a stented prosthetic valve for a percutaneous pulmonary valve replacement procedure is described in U.S. Patent Application Publication No. 2003/0199971 A1 and U.S. Patent Application Publication No. 2003/0199963 A1, both filed by Tower et al.

Although transcatheter delivery methods have provided safer and less invasive methods for replacing a defective native heart valve, leakage between the implanted prosthetic valve and the surrounding native tissue is a recurring problem. Leakage sometimes occurs due to the fact that minimally invasive and percutaneous replacement of cardiac valves typically does not involve actual physical removal of the diseased or injured heart valve. Rather, the replacement stented prosthetic valve is delivered in a compressed condition to the valve site, where it is expanded to its operational state within the native valve. Calcified or diseased native leaflets are forced open by the radial force of the stent frame of the prosthetic valve. These calcified leaflets may not completely conform to the stent frame, and any gaps between the stent frame and the native valve can be a source of paravalvular leakage ("PVL"). The closing pressure differential across the prosthetic valve can cause blood to leak through the gaps between the implanted prosthetic valve and the calcified anatomy. Such paravalvular leakage can be highly detrimental to the patient.

Because the aforementioned prosthetic valves are delivered via transcatheter procedures, there is an interest in reducing the profile of the compressed prosthetic valve during delivery while still providing a paravalvular leakage prevention wrap. The present disclosure addresses problems and limitations associated with the related art.

SUMMARY

As discussed above, stented prosthetic heart valves can leave paravalvular leakage pathways in some patients, particularly patients with very immobile or heavily calcified native valve leaflets. Disclosed embodiments include stented prosthetic heart valves (hereinafter "prosthetic valves") including a stent frame having an outer wrap or skirt to fill paravalvular leakage pathways. In disclosed embodiments, the position of the outer wrap is configured to reduce the profile of the compressed prosthetic valve during delivery while maximizing a thickness of the outer wrap.

Various embodiments include a prosthetic valve including a tubular stent frame having a plurality of stent frame support structures collectively defining an interior surface, an exterior surface and a plurality of cells. The prosthetic valve further includes valve leaflets secured to the interior surface of the stent frame. The valve leaflets defining a margin of attachment. The prosthetic valve including one or both of an outer paravalvular leakage prevention wrap ("outer wrap") and an inner skirt for supporting the valve leaflets. In various embodiments, the outer wrap is positioned entirely on one side of the margin of attachment. In various embodiments including an inner skirt supporting the valve leaflets, the outer wrap and the inner skirt are positioned to not overlap along a length of the stent frame. In this embodiment, the outer wrap is on one side (e.g., an inflow side) of the margin of attachment and the inner skirt is on the opposite side (e.g., an outflow side) of the margin of attachment. In this way, the outer wrap can have an increased thickness without increasing the profile of the compressed prosthetic valve during delivery. In various embodiments, the outer wrap includes at least two zones of varying thickness.

BRIEF DESCRIPTION OF THE DRAWINGS

FIG. 1 is a perspective view of an illustrative stented prosthetic heart valve that can be modified in accordance with the disclosure.

FIG. 2 is a front view of a stented prosthetic heart valve having an inner skirt and an outer wrap.

DETAILED DESCRIPTION

Figure 3:
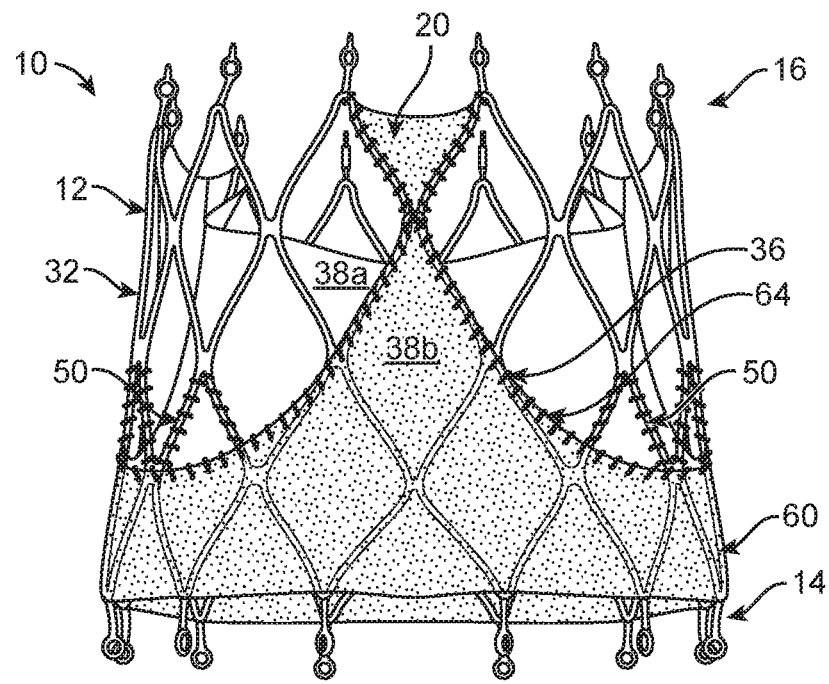
FIG. 3 is a side view of the stented prosthetic heart valve of FIG. 2.

Specific embodiments of the present disclosure are now described with reference to the figures, wherein like reference numbers indicate identical or functionally similar elements. As used herein with reference to a prosthetic heart valve, the term "outflow" is understood to mean downstream to the direction of blood flow, and the term "inflow" is understood to mean upstream to the direction of blood flow. Although the present disclosure has been described with reference to preferred embodiments, workers skilled in the art will recognize that changes can be made in form and detail without departing from the spirit and scope of the present disclosure.

Certain aspects of the present disclosure relate to transcatheter stented prosthetic heart valve delivery devices that retain a stented prosthetic heart valve (hereinafter "prosthetic valve") in a compressed arrangement during delivery to a target site and allow the prosthetic valve to expand and deploy at a target site. By way of background, general components of one non-limiting example of a stented prosthetic heart valve 10 with which the aspects of the present disclosure are useful are illustrated in FIG. 1.

After deployment of the prosthetic valve 10 at the target site, paravalvular leakage can occur. Therefore, prosthetic valves disclosed herein include an outer paravalvular leakage prevention wrap (hereinafter "outer wrap"), as will be discussed in detail below and illustrated in FIGS. 2-7.

Figures 1, 2:
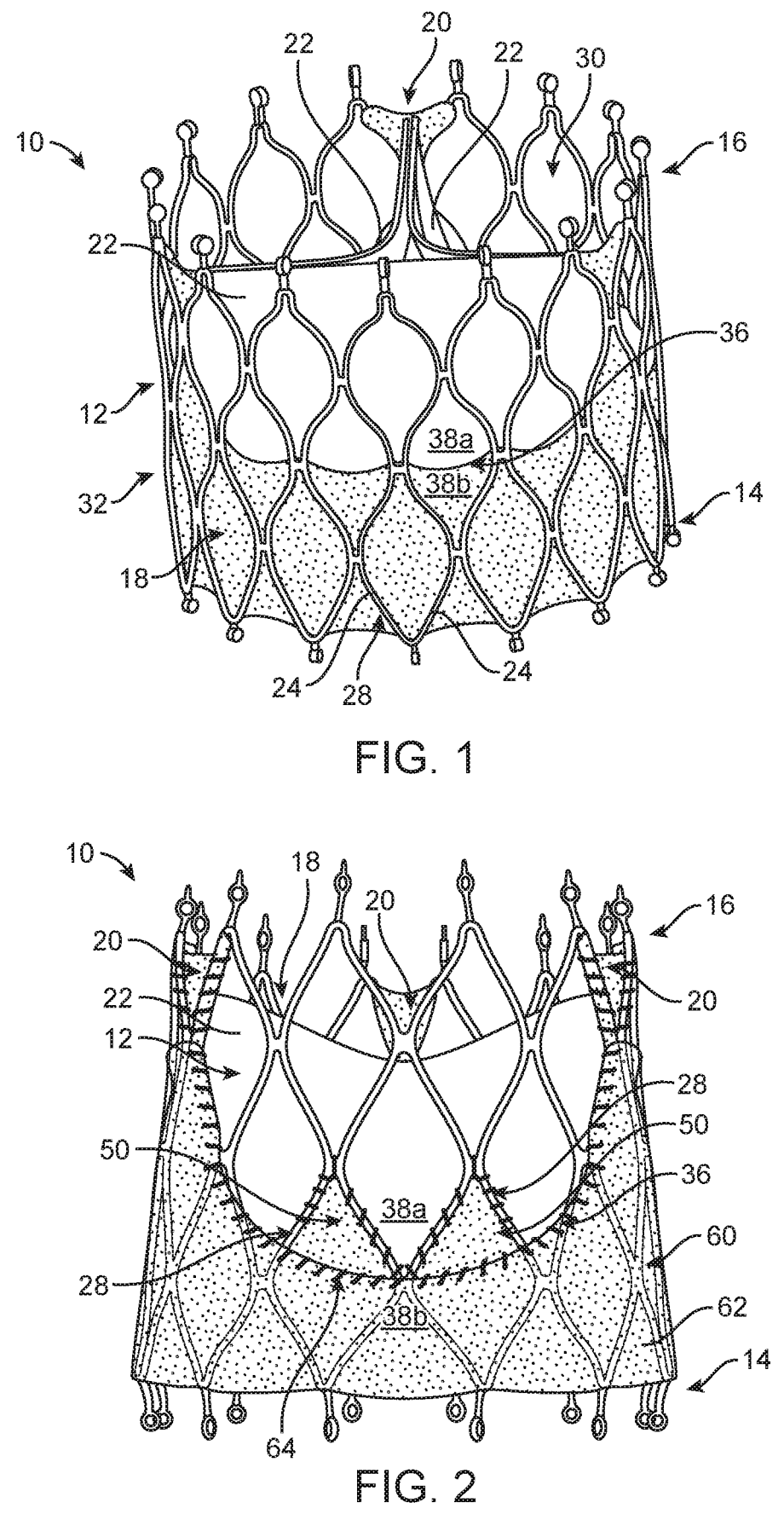

The prosthetic valve 10 has a compressed, delivery configuration and a normal, expanded arrangement as is shown in FIG. 1. The prosthetic valve 10 includes a tubular stent frame 12 having inflow and outflow ends 14, 16 and can assume any of the forms described herein, and is generally constructed so as to be self-expandable from the compressed arrangement to the normal, expanded deployed arrangement. In other embodiments, the stent frame 12 is expandable to the expanded arrangement by a separate device (e.g., a balloon internally located within the stent frame 12). A valve structure 18 is assembled to the stent frame 12 and provides two or more (typically three) leaflets 22. The valve structure 18 can assume any of the forms described herein, and can be assembled to the stent frame 12 in various manners, such as by sewing the valve structure 18 to the stent frame 12. Alternatively, the valve structure 18 can be secured to the stent frame 12 with an inner skirt as will be discussed below with respect to FIGS. 2-4.

As referred to herein, the stented prosthetic heart valve 10 or prosthetic valves that can be modified to incorporate outer wraps and inner skirts disclosed herein may assume a wide variety of different configurations. For example, the prosthetic heart valve can be a biostented prosthetic heart valve having tissue leaflets or a synthetic heart valve having polymeric, metallic, or tissue-engineered leaflets, and can be specifically configured for replacing any native heart valve. Thus, the prosthetic valve can be generally used for replacement of a native aortic, mitral, pulmonic, or tricuspid valve, for use as a venous valve, or to replace a failed bioprosthesis, such as in the area of an aortic valve or mitral valve, for example.

In general terms, the stents or stent frames 12 of the present disclosure include generally tubular support structures 24 defining a plurality of cells 28 and having an internal surface 30 and an exterior surface 32 (only one of the plurality of cells 28 and support structures 24 are labeled for ease of illustration). A valve structure 18 including commissure posts 20 supporting a plurality of valve leaflets 22 is secured to the internal surface 30. The valve leaflets 22 define a margin of attachment 36. The valve leaflets 22 can be formed from a variety of materials, such as autologous tissue, xenograft material, or synthetics as are known in the art. The valve leaflets 22 may be provided as a homogenous, biological valve structure, such as porcine, bovine, or equine valves. Alternatively, the valve leaflets 22 can be provided independent of one another (e.g., bovine or equine pericardial leaflets) and subsequently assembled to the support structure of the stent frame 12. In another alternative, the stent frame 12 and valve leaflets 22 can be fabricated at the same time, such as may be accomplished using high-strength nano-manufactured NiTi films produced at Advance BioProsthetic Surfaces (ABPS), for example. The stent frame 12 is generally configured to accommodate at least two (typically three) leaflets; however, replacement prosthetic valves of the types described herein can incorporate more or less than three leaflets.

In some constructions, the stent frame support structures 24 can be a series of wires or wire segments arranged such that they are capable of self-transitioning from a compressed or collapsed arrangement to the normal, radially expanded arrangement. The stent frame 12 of such an embodiment may be laser-cut from a single piece of material or may be assembled from a number of different components. The stent frame support structures 24 of the stent frame 12 can be formed from a shape-memory material such as a nickel titanium alloy (e.g., Nitinol™). With this material, the support structure is self-expandable from the compressed arrangement to the normal, expanded arrangement, such as by the application of heat, energy, and the like, or by the removal of external forces (e.g., compressive forces). This stent frame 12 can be compressed and re-expanded multiple times without damaging the stent frame support structures 24. These stent frame support structures 24 are arranged in such a way that the stent frame 12 allows for folding or compressing or crimping to the compressed arrangement in which the internal diameter is smaller than the internal diameter when in the normal, expanded arrangement. In the compressed arrangement, such a stent frame 12 with attached valve leaflets 22 can be mounted onto a delivery device. One example of a suitable delivery device is disclosed in U.S. Pat. No. 8,579,963 to Tabor, the disclosure of which is herein incorporated by reference in its entirety. The stent frame support structures 24 are configured so that they can be changed to their normal, expanded arrangement when desired, such as by the relative movement of one or more sheaths relative to a length of the stent frame 12 as defined between the inflow and outflow ends 14, 16.

The prosthetic valve 10 is configured for replacing an aortic valve. Alternatively, other shapes are also envisioned, adapted for the specific anatomy of the valve to be replaced (e.g., prosthetic valves in accordance with the present disclosure can alternatively be shaped and/or sized for replacing a native mitral, pulmonic, or tricuspid valve). Regardless, the valve structure 18 can be arranged to extend less than an entire length of the stent frame 12. In particular, the valve structure 18 can be assembled to, and extend along, the inflow end 14 of the prosthetic valve 10, whereas the outflow end 16 can be free of the valve structure 18 material. A wide variety of other constructions are also acceptable and within the scope of the present disclosure. For example, the valve structure 18 can be sized and shaped to extend along an entirety, or a near entirety, of a length of the stent frame 12.

Figure 4:
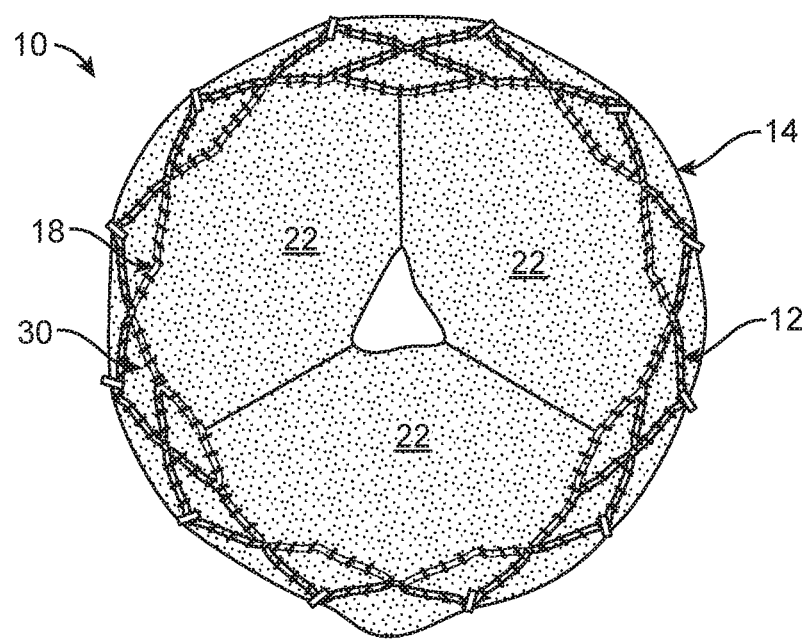
FIG. 4 is a bottom view of the stented prosthetic heart valve of FIGS. 2-3.

Turning now also to FIGS. 2-4, the prosthetic valve 10 can include an optional inner skirt 50 attached to the internal surface 30 of the stent frame 12 that interconnects and supports the valve leaflets 22 with respect to the stent frame 12. The inner skirt 50 can comprise treated pericardial tissue or biocompatible synthetic material such as bioabsorbable mesh (e.g., poly(glycerol-co-sebacate), polylactic acid and polycaprolactone), for example. In example embodiments, the inner skirt 50 is positioned within a portion of an area of at least one cell 28. As shown, the inner skirt 50 is positioned on or "above" (i.e. on an outflow side 38a) the margin of attachment 36, proximate the outflow end 16 of the stent frame 12.

The prosthetic valve 10 can further include an outer wrap 60 for paravalvular sealing to prevent leakage of the implanted prosthetic valve 10 around the stent frame 12. The outer wrap 60 comprises a body 62 made of treated pericardial tissue or biocompatible synthetic material such as woven or knit fabric (e.g., PET, UHMWPE, Polypropylene), or bioabsorbable mesh (e.g., poly(glycerol-co-sebacate), polylactic acid and polycaprolactone), for example. The body 62 can also be constructed of more than one material, as desired. In one example embodiment, the outer wrap 60 is arranged on the exterior surface 32 of the stent frame 12 at a position on or "below" (i.e. on an inflow side 38b) the margin of attachment 36. In various embodiments, a boundary or edge 64 of the outer wrap 60 can be aligned with or the same as the margin of attachment 36. To reduce the profile of the compressed prosthetic valve 10 while allowing for an increased thickness of the outer wrap 60, in various embodiments, the inner skirt 50 and the outer wrap 60 do not overlap along a length of the stent frame 12. In some embodiments, the inner skirt 50 and the outer wrap 60 may be adjacent or touching at a joint boundary (e.g., the margin of attachment 36) but, in the illustrated embodiment, the inner skirt 50 and the outer wrap 60 do not overlap.

Figure 5:
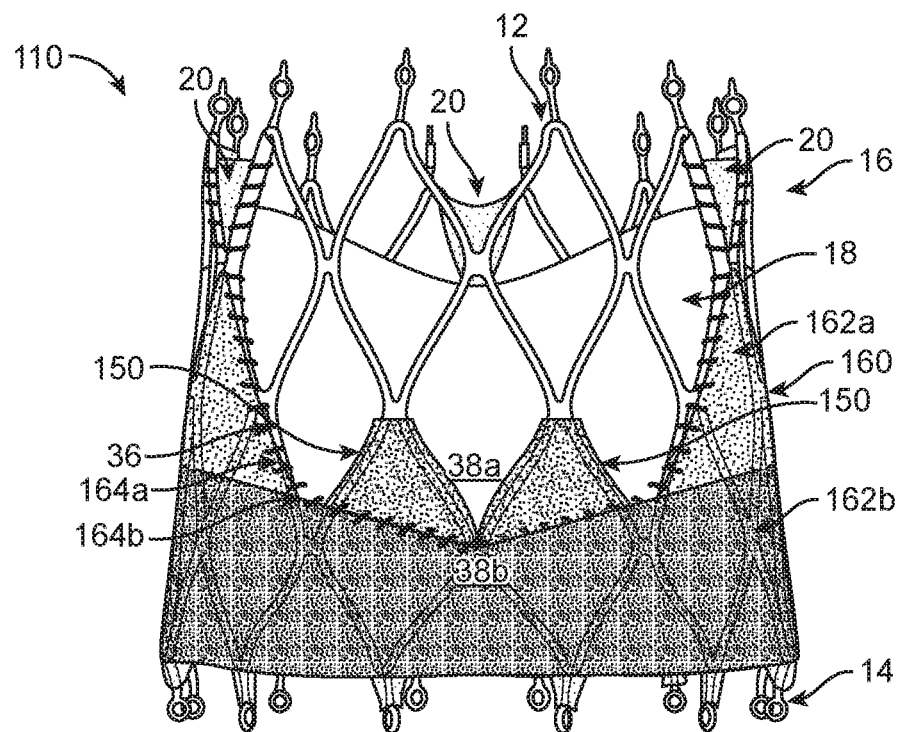
FIG. 5 is a front view of an alternate stented prosthetic heart valve having an inner skirt and an outer wrap having zones of varying thickness.

Turning now also to FIG. 5, which illustrates an alternate stented prosthetic heart valve 110. The stented prosthetic heart valve 110 is similar to that shown and described with respect to FIGS. 2-4 but includes an alternate outer wrap 160. In this embodiment, the outer wrap 160 has at least two zones 162a, 162b of varying thickness. It is envisioned that the portion(s) or zone(s) 162a of the outer wrap 160 that are not specifically targeting paravalvular leakage reduction will have a smaller thickness as compared to zone(s) 162b that are of higher paravalvular leakage concern (for example the region between the valve nadir and the inflow end). In this illustrated embodiment, the outer wrap 160 has a first zone 162a and a second zone 162b. The second zone 162b is generally a band wrapping along the circumference of the frame 12 proximate the inflow end 14. In one example embodiment, the outer skirt 160 could be 0.1 mm thick in the first zone 162a and 0.3 mm thick in the second zone 162b. The second zone 162b could be comprised of a layer of material positioned on top of first layer of material to form a double layer. Alternatively, the second zone 162b could be a separate, thicker material as compared to the first zone 162a to provide an increased thickness. In such an embodiment, the first and second zones 162a, 162b can be attached by sutures or the like to form a seam where the two butt together or by using fusing techniques if polymeric materials are used, for example. As with the prior embodiment, both zones 162a, 162b have respective boundaries 164a, 164b that are positioned on one side 38b of the margin of attachment 36. Moreover, the prosthetic heart valve 110 can further optionally include an inner skirt 150 configured as disclosed with respect to the inner skirt 50 of FIGS. 2-4.

Figure 6:
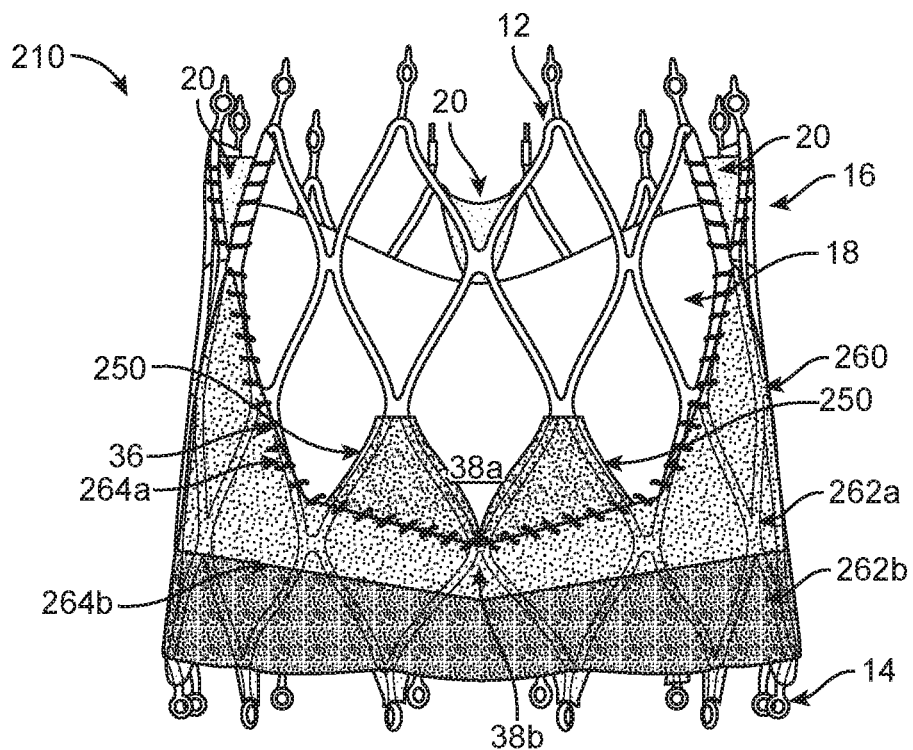
FIG. 6 is a front view of a further alternate stented prosthetic heart valve having an inner skirt and an outer wrap having zones of varying thickness.

FIG. 6 illustrates yet another stented prosthetic heart valve 210 having an outer wrap 260 including at least two zones 262a, 262b of varying thickness. In this illustrated embodiment, the outer wrap 260 has a first zone 262a and a second zone 262b. The second zone 262b is a band wrapping along the circumference of the frame 12 proximate the inflow end 14. The outer wrap 260 can be similarly configured in that the variance in thickness can be obtained in many ways, either via different materials or layering of materials. As with prior disclosed embodiments, both zones 262a, 262b have respective boundaries 264a, 264b that are positioned on one side 38b of the margin of attachment 36. Moreover, the prosthetic heart valve 210 can further optionally include an inner skirt 250 configured as disclosed with respect to the inner skirt 50 of FIGS. 2-4.

Figure 7:
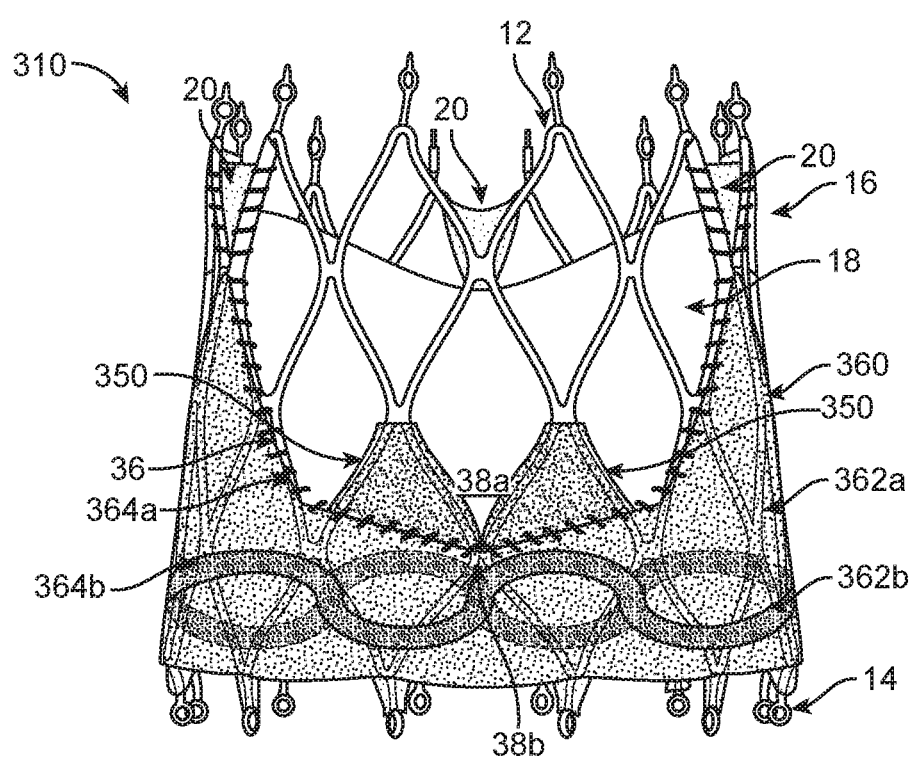
FIG. 7 is a front view of yet another stented prosthetic heart valve having an inner skirt and an outer wrap having zones of varying thickness.

FIG. 7 illustrates yet another stented prosthetic heart valve 310 having an outer wrap 360 including at least two zones 362a, 362b of varying thickness. In this illustrated embodiment, the outer wrap 360 has a first zone 362a and a second zone 362b. The second zone 362b is a generally sinusoidal band wrapping along the circumference of the frame 12 proximate the inflow end 14. The outer wrap 360 can be similarly configured in that the variance in thickness can be obtained in many ways, either via different materials or layering of materials. As with prior disclosed embodiments, both zones 362a, 362b have respective boundaries 364a, 364b that are positioned on one side 38b of the margin of attachment 36. Moreover, the prosthetic heart valve 310 can further optionally include an inner skirt 350 configured as disclosed with respect to the inner skirt 50 of FIGS. 2-4.

Although the present disclosure has been described with reference to preferred embodiments, workers skilled in the art will recognize that changes can be made in form and detail without departing from the spirit and scope of the present disclosure.

What is claimed is:

1. A stented prosthetic heart valve comprising:
    a tubular stent frame having a plurality of stent frame support structures collectively defining a plurality of cells, an interior surface and an exterior surface of the stent frame;
    a valve structure including valve leaflets disposed within and secured to the stent frame, the valve leaflets defining a margin of attachment; wherein the margin of attachment defines a boundary between an inflow side and an outflow side of the margin of attachment; wherein the valve structure includes first, second and third commissure posts positioned between and supporting adjacent valve leaflets; and
    an outer wrap generally encircling the exterior surface of the stent frame; wherein the outer wrap is positioned entirely on the inflow side of the margin of attachment; wherein the outer wrap has a U-shaped boundary that is aligned with the margin of attachment, the U-shaped boundary spanning from the first commissure post to the second commissure post.

2. The stented prosthetic heart valve of claim 1, further comprising an inner skirt supporting the valve leaflets on the interior surface of the stent frame.

3. The stented prosthetic heart valve of claim 2, wherein the inner skirt spans less than an area of one respective cell.

4. The stented prosthetic heart valve of claim 2, wherein the inner skirt and the outer wrap collectively span an area of one respective cell.

5. The stented prosthetic heart valve of claim 2, wherein the inner skirt is positioned entirely on the outflow side of the margin of attachment.

6. The stented prosthetic heart valve of claim 1, wherein the outer wrap includes at least two zones of varying thickness.

7. A stented prosthetic heart valve comprising:
    a tubular stent frame having a plurality of stent frame support structures collectively defining a plurality of cells, an interior surface and an exterior surface of the stent frame;

valve leaflets disposed within and secured to the stent frame and defining a margin of attachment; wherein the valve structure includes a plurality of commissure posts; and an outer wrap generally encircling the exterior surface of the stent frame; wherein the outer wrap has a U-shaped boundary that is aligned with the margin of attachment, the U-shaped boundary spanning from one of the plurality of commissure posts to one adjacent commissure post.

8. The stented prosthetic heart valve of claim 7, further comprising an inner skirt supporting the valve leaflets on the interior surface of the stent frame.

9. The stented prosthetic heart valve of claim 8, wherein the inner skirt spans less than an area of one respective cell.

10. The stented prosthetic heart valve of claim 8, wherein the inner skirt and the outer wrap collectively span an area of one respective cell.

11. The stented prosthetic heart valve of claim 8, wherein the margin of attachment defines a boundary between an inflow side and an outflow side of the margin of attachment; wherein the inner skirt is positioned entirely on the outflow side of the margin of attachment.

12. The stented prosthetic heart valve of claim 11, wherein the inner skirt is aligned with the margin of attachment.

13. The stented prosthetic heart valve of claim 8, wherein the outer wrap has at least two zones of varying thickness.

14. The stented prosthetic heart valve of claim 7, wherein the outer wrap includes at least two zones of varying thickness.

15. A stented prosthetic heart valve comprising:
a tubular stent frame having a plurality of stent frame support structures collectively defining a plurality of cells, an interior surface and an exterior surface of the stent frame;
a valve structure including valve leaflets disposed within and secured to the stent frame and defining a margin of attachment;
an outer wrap generally encircling the exterior surface of the stent frame, the outer wrap having at least two zones of varying thickness; and
an inner skirt supporting the valve leaflets on the inside surface of the stent frame;
wherein the outer wrap and the inner skirt are positioned to not overlap along a length of the stent frame.

16. The stented prosthetic heart valve of claim 15, wherein the margin of attachment defines a boundary between an inflow side and an outflow side of the margin of attachment; wherein the outer wrap has a boundary that is aligned with the margin of attachment.

17. The stented prosthetic heart valve of claim 15, wherein the inner skirt spans less than an area of one respective cell.

18. The stented prosthetic heart valve of claim 15, wherein the inner skirt and the outer wrap collectively span an area of one respective cell.

19. The stented prosthetic heart valve of claim 15, wherein one zone of varying thickness is a sinusoidal band extending around the outer wrap.

20. The stented prosthetic heart valve of claim 15, wherein the valve structure includes first, second and third commissure posts positioned between and supporting adjacent valve leaflets; wherein the outer wrap has a U-shaped boundary that is aligned with the margin of attachment, the U-shaped boundary spanning from the first commissure post to the second commissure post.

* * * * *

UNITED STATES PATENT AND TRADEMARK OFFICE
CERTIFICATE OF CORRECTION

| | |
|---|---|
| PATENT NO. | : 10,729,542 B2 |
| APPLICATION NO. | : 15/792991 |
| DATED | : August 4, 2020 |
| INVENTOR(S) | : Elliot Howard et al. |

It is certified that error appears in the above-identified patent and that said Letters Patent is hereby corrected as shown below:

In the Claims

In Column 7, Line 1, Claim 1, "valve leaflets disposed within and secured to the stent" should read --a valve structure including valve leaflets disposed within and secured to the stent--.

In Column 8, Line 7, Claim 15, "an inner skirt supporting the valve leaflets on the inside" should read --an inner skirt supporting the valve leaflets on the interior--.

Signed and Sealed this
Second Day of January, 2024

Katherine Kelly Vidal
*Director of the United States Patent and Trademark Office*